United States Patent [19]

Diederich et al.

[11] Patent Number: 4,500,309
[45] Date of Patent: Feb. 19, 1985

[54] METHOD FOR REGIONAL ANTICOAGULATION DURING EXTRACORPOREAL DIALYSIS

[75] Inventors: Dennis A. Diederich, Overland Park; Thomas B. Wiegmann, Fairway; Robert V. Pinnick, Overland Park, all of Kans.

[73] Assignee: The Kansas University Endowment Association, Lawrence, Kans.

[21] Appl. No.: 375,890

[22] Filed: May 7, 1982

[51] Int. Cl.³ .............................................. A61M 1/03
[52] U.S. Cl. ................................ 604/5; 128/DIG. 3; 210/646
[58] Field of Search ........................................ 604/4–6; 128/DIG. 3; 210/321.3, 645–647, 927

[56] References Cited

U.S. PATENT DOCUMENTS

| 3,482,575 | 12/1969 | Claff et al. | 604/4 |
| 3,483,867 | 12/1969 | Markovitz | 604/5 |
| 4,329,986 | 5/1982 | Babb | 210/645 X |
| 4,381,004 | 4/1983 | Babb | 604/5 |

FOREIGN PATENT DOCUMENTS 2152355  4/1973  Fed. Rep. of Germany .......... 604/4

Primary Examiner—Dalton L. Truluck
Attorney, Agent, or Firm—Schmidt, Johnson, Hovey & Williams

[57] ABSTRACT

An improved hemodialysis method (which may optionally include a hemoperfusion step) including regional extracorporeal citrate anticoagulation is disclosed which permits complete elimination of conventional heparin treatment and possible consequent medical complications from heparin use. The method preferably comprises removing blood from a patient at a level of at least about 80 milliliters per minute, infusing citrate anticoagulant into the blood at a level of up to about 10 millimoles of citrate anion per liter of blood, treating the blood (e.g., by dialysis and hemoperfusion if desired), thereafter infusing a calcium compound into the blood to restore proper calcium ion level and coagulative properties, and returning the blood to the patient. A calcium-free acetate or bicarbonate dialysate is advantageously employed. A charcoal perfusion filter can optionally be used in conjunction with the dialyzer apparatus.

12 Claims, 1 Drawing Figure

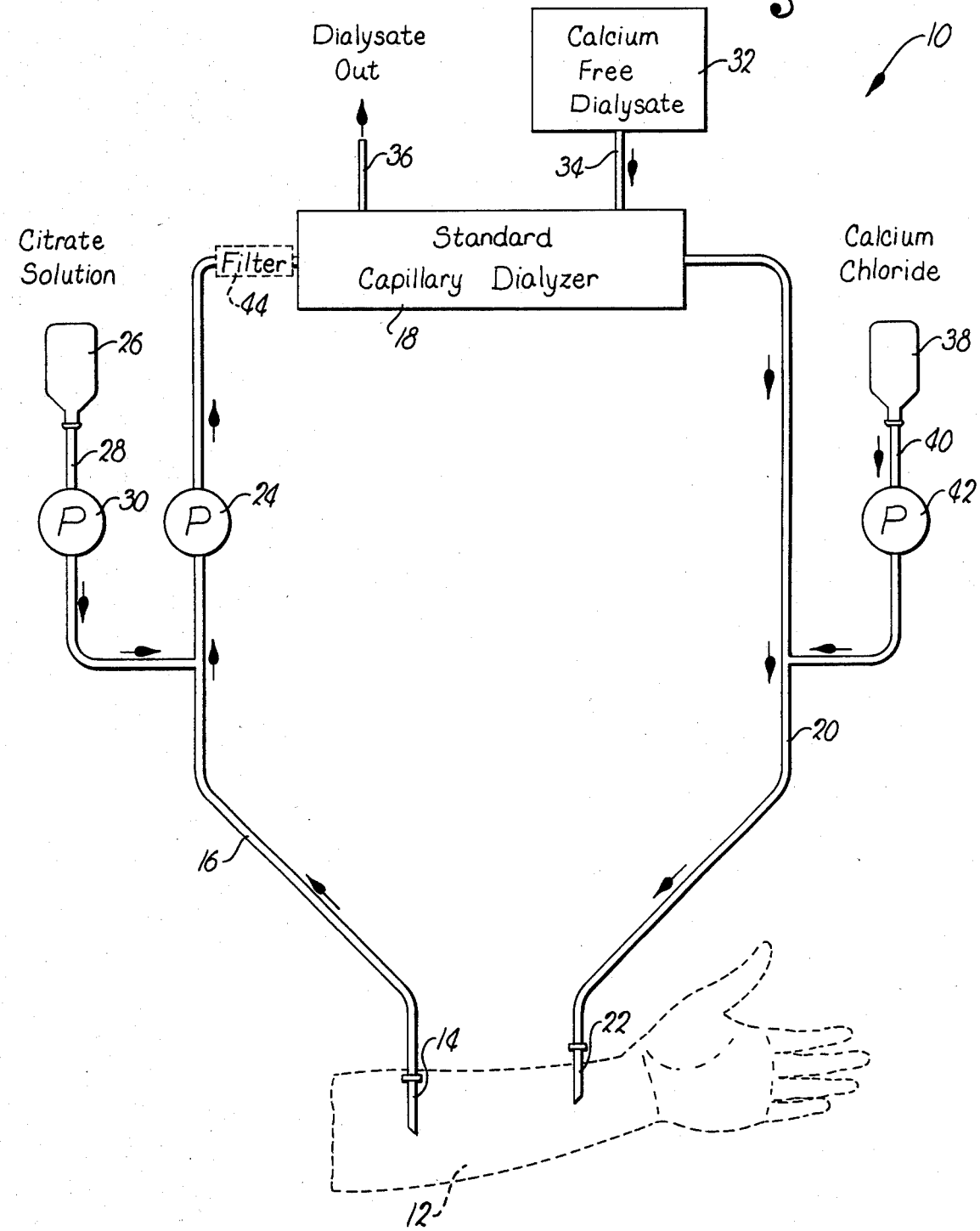

METHOD FOR REGIONAL ANTICOAGULATION DURING EXTRACORPOREAL DIALYSIS

BACKGROUND OF THE INVENTION

1. Field of the Invention

The present invention is concerned with an improved extracorporeal hemodialysis blood treatment method, wherein use is made of a technique for effective regional, extracorporeal anticoagulation of the patient's blood. More particularly, it is concerned with such an improved method which involves infusion of a citrate anticoagulant into the blood at a relatively low level, followed by treatment of the blood, subsequent infusion of a calcium compound into the blood in order to restore the coagulative properties thereof, and final return of the blood to the patient.

2. Description of the Prior Art

In the past few decades extracorporeal blood treatments such as hemodialysis and charcoal resin hemoperfusion have become relatively commonplace. In such techniques, blood is withdrawn from the patient, treated as desired, and returned to the patient. For example, in hemodialysis, the withdrawn blood is passed through a dialyzing unit along with an acetate or bicarbonate-based dialysate. In the dialyzer, toxins in the blood pass through semi-permeable membranes separating the blood and dialysate, in order to reduce the toxin concentration in the patient's blood. Hemoperfusion on the other hand basically involves passing the patient's blood through a specially designed charcoal resin filter prior to return of the blood to the patient.

In extracorporeal blood treatments of the type outlined above, anticoagulation of the blood is generally considered a necessary prerequisite to avoid clotting. That is to say, if the patient's blood is withdrawn in its normal condition, in passage through treatment apparatus the blood clots which form effectively impair treatment. The conventional technique for anticoagulation of blood has involved the use of heparin injection of the patient. The problems with heparin-based anticoagulation are generally twofold, namely, systemic anticoagulation of the patient and destruction of blood elements (platelets and leukocytes) resulting from deleterious interactions of blood cells with the dialyzing membrane or charcoal resins.

Systemic anticoagulation of patients is oftentimes quite undesirable because of hemorrhagic tendencies so frequently encountered in uremic or otherwise acutely ill patients. Moreover, hemorrhagic complications are serious and limiting problems encountered in actively bleeding renal failure (acute or chronic) patients, in post operative patients (especially cardiovascular procedures), in the ill septic patient and in acute hepatic failure. In the past, there have been attempts to limit the systemic effects of heparin by "regional" use of protamine to neutralize heparin in blood being returned to the patient and infusing small continuous doses of heparin (limited systemic heparinization) as opposed to loading doses. The expedients have however failed to circumvent hemorrhagic complications. Indeed, in a recent study addressing this problem, these two methods (heparin + protamine vs. limited systemic heparinization) hemorrhagic complications were noted in 10 to 19 percent of a group of patients with renal failure (*Kidney Internat.*, 16:513–18, 1979).

Another problem occurring with conventional hemodialysis and in particular with resin hemoperfusion is the development of thrombocytopenia and leukopenia. A complement mediated blood cell membrane-resin/dialyzer membrane interaction leads to cell damage and in vivo sequestration of injured cells. Life threatening thrombocytopenia resulting from charcoal perfusion in hepatic failure necessitates platelet transfusions. Granulocytopenia and thrombocytopenia resulting from hemodialysis and charcoal resin hemoperfusion are of special concern in the septic patient, the acute bleeding uremic patient, and in post operative patients with renal failure.

It is also known that citrate anion is an extremely effective anticoagulative substance, which operates by complexing with calcium ion in the blood. In fact, a study has heretofore been undertaken to investigate with possibility of using citrate anticoagulants in the context of hemodialysis ("Regional Anticoagulation During Hemodialysis Using Citrate", Morita et al., *The American Journal of the Medical Sciences*, July, 1961, pp. 72–82. In the Morita et al. study, citrate anticoagulant was added to blood withdrawn from a patient, followed by dialysis of the blood and return thereof to the patient. However, the techniques described in this article were fraught with a number of serious problems, and were never adopted.

Specifically, Morita et al. described the use of trisodium citrate.$2H_2O$ as a regional anticoagulant to replace heparin during hemodialysis and showed significant increases in the coagulation time of the blood exiting the hemodialyzer. However, use of the trisodium citrate gave unacceptable elevations of arterial plasma sodium (hypernatremia); in addition, because the dialysis treatment removed calcium ion from the patient's blood, hypocalcemia resulted. In an attempt to resolve these problems, Morita et al. attempted to employ monosodium dihydrogen citrate, and to add calcium ion at the dialyzer. While the use of a monosodium dihydrogen citrate did reduce the hypernatremia problem, its low pH (3.8) and the amount of free citric acid added (about 1000 milliequivalents for 6 hour treatment), blood acidosis problems were encountered. Furthermore, addition of calcium ion at the dialyzer (through use of a calcium-containing dialysate) caused undue complexation with the added citrate, thereby requiring still further initial citrate infusion. Thus, the solutions attempted by Morita et al. led only to further unacceptable difficulties.

In short, while the Morita et al. work demonstrated that citrate anion could be used as an effective anticoagulant during extracorporeal hemodialysis, the techniques therein employed created serious and even life-threatening problems.

In another recent development of Babb et al., reported in *Artificial Organs*, Apr. 7, 1979, pp. 470ff. and entitled "Design Criteria For An Extracorporeal Chemotherapeutic System To Continuously Modify Sickle Cell Hemoglobin", a technique was described for a cyanate treatment of the blood of sickle cell patients. As an adjunct to this treatment, an anticoagulant system was described wherein trisodium citrate was infused into withdrawn blood at a level of 10.2 millimoles citrate anion per liter of blood, followed by cyanate treatment, dialysis to remove cyanate, infusion of $CaCl_2$ and heparin, and return of the blood to the patient. However, this sickle cell treatment necessarily involves blood flows (up to 70 ml/min.) which are excessively slow for conventional hemodialysis or hemoperfusion;

moreover, use of heparin is objectionable for the reasons outlined above.

SUMMARY OF THE INVENTION

The present invention overcomes the problems noted above and provides a truly effective regional extracorporeal method of blood anticoagulation, using citrate anion. Broadly speaking, the invention involves hemodialysis blood treatment (which may also include a hemoperfusion step) wherein blood is withdrawn from a patient, treated, and returned to the patient. During extracorporeal passage of blood through the circuit and treating apparatus therefor, a citrate anion-containing anticoagulant substance is infused into the blood; the bulk of citrate anion complexed with calcium is thereafter removed from the blood by the dialyser apparatus; and prior to return of the blood to the patient, a calcium compound is infused into the blood in an amount to reestablish a normal level of calcium ion in the blood.

In the context of a conventional hemodialysis to remove toxins, the blood is withdrawn from the patient at a rate of at least about 80 milliliters per minute, and more preferably at a rate of from about 100 to 300 milliliters per minute, and most preferably at a rate of about 150 to 250 milliliters per minute. Such withdrawn blood is continuously infused with a citrate anticoagulant, most preferably trisodium citrate. $2H_2O$, and this substance is advantageously the sole anticoagulant employed. The anticoagulant should be infused at a level to provide up to about 10 millimoles of citrate anion per liter of bood, and more preferably at a level to provide up to about 8 millimoles of citrate anion per liter of blood. Inasmuch as it is desirable to minimize the amount of citrate anion infused (in order to lessen the loading on the downstream dialyzer and to prevent undue loading of the patient with liquid), it has been found that the anticoagulant should be infused at a level within the range of from about 2 to 8 millimoles of citrate anion per liter of blood, and most preferably at a level of about 2 to 6 millimoles of citrate anion per liter of blood.

In the dialyzer (which can be of any conventional construction) the dialysate is employed for removing toxins from the blood. In order to minimize the amount of citrate needed for the overall procedure, it is highly advantageous to use a dialysate which is essentially calciumfree. That is to say, calcium in the dialysate will complex with citrate, thus requiring additional citrate infusion. The dialysate can be either an acetate or bicarbonate-based solution, as those skilled in the art will readily perceive. It is also advisable to employ a dialysate which is isotonic relative to the blood.

If desired, a charcoal resin hemoperfusion filter can be employed in conjunction with the methods of the invention. Such filters are well known, and when used the only recommended changes in procedure are to increase the amount of citrate anion added, as compared with a straight-forward hemodialysis treatment.

BRIEF DESCRIPTION OF THE DRAWING

The single FIGURE is a schematic illustration of apparatus useful in conjunction with the present invention, for hemodialysis with and without hemoperfusion of a patient's blood.

DESCRIPTION OF THE PREFERRED EMBODIMENTS

Turning first to the drawing, treatment apparatus 10 is illustrated in the FIGURE for hemodialysis with or without hemoperfusion of a patient's blood, withdrawn from a limb such as arm 12. The overall apparatus 10 includes an arterial needle 14 operatively coupled to an arterial blood line 16, the latter being ultimately coupled to a standard capillary dialyzer 18. A return or venous blood line 20 is connected to the output end of dialyzer 18, and to a venous needle 22. It will be observed that the needles 14 and 22 are respectively inserted into the patient's arm 12 at appropriate locations for withdrawal and return of blood.

A blood pump 24 of known construction is interposed within line 16 for the purpose of moving blood through the circuit defined by line 16, dialyzer 18 and line 20.

A supply of citrate anticoagulant solution 26 also forms a part of overall apparatus 10, and is connected to a delivery line 28 having a pressure insensitive occlusive roller pump 30 interposed therein. The line 28 is connected to line 16 as illustrated, for the purpose of continuous infusion of the citrate solution into the blood withdrawn from the patient. Advantageously, the connection of line 28 with line 16 should be as close as possible to needle 14 (e.g., within six inches) so as to minimize extracorporeal clotting).

As noted, dialyzer 18 is of conventional construction, and can be, for example, a Cordis Dow C-D 4000 capillary dialyzer. A supply of calcium-free dialysate 32 is connected via a line 34 to the dialyzer 18, whereas an exit line 36 is provided for withdrawal of used dialysate from the apparatus. The dialysate within supply 32 can be of any known type, such as an acetate or bicarbonate-based solution.

A supply 38 of calcium ion-containing material (e.g., $CaCl_2$) is coupled for infusion with venous line 20 through a delivery line 40. A pressure-insensitive pump 42 is interposed within line 40 for the purpose of controlling infusion of the substance into venous line 20. Here again, the connection between lines 40 and 29 should be as close as possible to the needle 22 (e.g., within six inches).

In those instances where it is desired to perform a hemoperfusion operation, a standard hemoperfusion filter 44 can be employed. In this regard, a filter is placed in series between the end of line 16 and dialyzer 18, as illustrated by the dotted line representation of the FIGURE.

It should be understood that the apparatus depicted in the drawing is only schematically represented, and that certain of the components form parts of conventional dialysis machines. In addition, a number of well known controls and monitors associated with such equipment have been omitted for sake of clarity.

However, it has been determined that certain additional controls, not found in conventional dialyzer apparatus, should be used in conjunction with apparatus 10. For example, appropriate monitoring devices should be employed with the citrate and calcium ion addition structure, to ensure that citrate and calcium ion are in fact bein added during the hemodialysis operation. In addition, the blood pump 24 should be monitored, along with dialyzer 18, the latter for the purpose of determining when and if the dialyzer is in a bypass mode, i.e., where blood is passing through the apparatus but is not being dialyzed.

In the event that the citrate supply is exhausted or interrupted, the citrate pump 30, calcium ion pump 42 and blood pump 24 should be immediately and simultaneously shut down. When the citrate supply problem has been solved, all of the aforementioned pumps should be restarted simultaneously.

If the calcium supply is exhausted or interrupted, the calcium ion pump 42 should be immediately shut down, along with blood pump 24. However, there should be a delay, say 60 seconds, after shut down of the pumps 42, 24, until the citrate pump 30 is shut down. This permits the line 16 upstream of the connection thereof with line 28 to be purged through the medium of the citrate pump. If the calcium ion supply problem is solved in less than 60 seconds, the blood pump and calcium ion pump can be restarted simultaneously. If solving this problem requires more than 60 seconds, all pumps should be started simultaneously.

In the event that the blood pump 24 is shut down for any reason, the calcium ion pump 42 should be immediately shut down, but a delay of 60 seconds or the like should be employed prior to shut down of the citrate pump 30. If the blood pump problem is solved within 60 seconds, the blood pump and calcium ion pump should be restarted simultaneously; if solving problem takes more than 60 seconds, all pumps should be resumed together.

In the event that dialyzer apparatus 18 goes into a bypass mode, it will be understood that citrate ion is not being removed. Accordingly, in the event of this occurrence, the calcium ion pump should be shut down immediately whereas the blood pump should be shut down only after a delay of, e.g., 3 minutes. This permits sufficient time to adjust the dialyzer apparatus 18 without shutting the entire apparatus 10 down. This for the reason that bypass operations are relatively common, and a patient would be in no danger for a short period while attempts are made to put the dialyzer apparatus back on stream. In addition, the citrate pump should be shut down after a period of time following shut down of the blood pump, e.g., 4 minutes after monitoring of a bypass condition in the dialyzer 18.

If the bypass problem is solved within the first delay period mentioned, the calcium ion pump 42 can simply be resumed. If the bypass problem is solved after the first delay and consequent shut down of the blood pump, but prior to shut down of the citrate pump, it is only necessary to resume the blood pump and calcium ion pump simultaneously. If the bypass operation can only be rectified after a relatively long period, all of the pumps should be resumed simultaneously.

Those skilled in the art will readily appreciate that the foregoing control sequences can be easily established using conventional sensors and control circuitry.

OPERATION

To carry out a hemodialysis using the apparatus illustrated in the FIGURE, blood is withdrawn from the patient and the inflow of citrate is simultaneously initiated. Blood flow rate is increased over the first 5-10 minutes of the procedure to 250 milliliters per minute maximum with or without charcoal perfusion. Calcium chloride replacement is begun after flow through the system is commenced. Both the citrate and calcium pumps, once calibrated, deliver reproduceable volumes that are insensitive to positive or negative pressures.

Whole blood clotting time of the patient tends to decrease with time while that of the citrated blood remains beyond 30 minutes. In the event that clotting occurs in the extracorporeal system, resistance to flow through the capillary dialyzer is reflected by the arterial line pressure of monitor of the machine; similarly, clotting in the venous return line elevates venous pressure which is also continuously monitored.

Because approximately 300 milliliters of volume (citrate) is added to the system per hour (1200 cc/hour with charcoal hemoperfusion), ultrafiltration is advantageously employed. In the case of the preferred C-D 4000 dialyzer, 1500-2000 cc/hour are readily removed by ultrafiltration. Thus, even with the larger volume of citrate employed with charcoal hemoperfusion, the additional volume can be easily removed.

Further details of the preferred procedures are set forth below:

1. Amount of Citrate Required

It has been found that the addition of 2.5 mM of citrate anion to the blood (final concentration) will prolong whole blood clotting (in vitro) at least twofold; 10 mM citrate effects the clotting time of infinity. Therefore, in most procedures, a 2.5 mM citrate (final) for hemodialysis and 5-10 mM citrate for hemodialysis plus charcoal hemoperfusion is sought.

2. Calcium Replacement

The clearance of calcium by the capillary dialyzer under a wide variety of circumstances (i.e., flow rates, presence of protein and of citrate and pH) has ben measured, and a reproduceable maximum clearance of $75 \pm 5$ ml/minute is observed above blood flow rates of 100 ml/minute. Thus, a constant amount of calcium is removed per minute above a flow rate of 100 ml/minute. For instance, serum calcium is 10 mg/dl, clearance is 70 ml/minute, and 7 mg. of calcium is removed per minute at 100-250 ml/minute blood flow rate. In practice, 7.0 mg of calcium is reinfused per minute, and serum calcium remains extremely stable under these conditions. Moreover, because use is made of a calcium-free dialysate, any excess accumulation of calcium in the patient is dialyzed off very readily in the dialyzer 18.

3. Amount of Citrate Infused Into the Patient

The clearance of citrate at a blood flow rate of 200 ml/minute with a capillary dialyzer is approximately 125-150 ml/minute. With 2.5 mM citrate, this would mean that blood returned to the patient would contain up to 1 mM of citrate per liter of blood. During a typical dialysis procedure, 50 liters of blood (12 liters per hour) will be dialyzed; this would mean 50 mM of citrate were infused at a maximum. Standard blood used for transfusion contains 13 mM citrate of comparison. Citrate intoxication, consisting primarily of consequences of decreased ionized calcium, becomes a concern when citrate infusion rates above 1 mg/Kg/min are employed in acute situations; however, the described infusion rates are significantly below this level, and by all available criteria the amount of citrate returned to the patient in the described procedure is acceptable.

4. Patient Selection

In the case of hemodialysis, patients at risk for hemorrhage and thus particularly suited for citrate extracorporeal anticoagulation, include uremic patients, post-operative and post-traumatic renal failure patients, patients with sepsis and renal failure (particularly those receiving large doses of drugs that inhibit platelet function), and patients with combined hepatic and renal failure. Finally, patients with severe thrombocytopenia or pancytopenia needing dialysis can be dialyzed to good effect using the techniques of the instant invention.

Charcoal hemoperfusion with hemodialysis exacts a heavy price on circulating WBC and platelets. In the patient with acute hepatic failure, risk of hemorrhage from charcoal treatment rises tremendously. The drop in WBC and platelets with charcoal hemoperfusion is completely prevented by the citrate anticoagulation methods hereof. Just as important is the fact that no systemic anticoagulation of the patient is needed. These features of the citrate anticoagulation of the invention make it the technique of choice for carrying out detoxification hemoperfusions.

The following Example will illustrate the features of the present invention:

EXAMPLE

In preparartive procedures, the following were prepared:

(1) An isotonic anticoagulant solution (0.1M) was prepared using trisodium citrate (U.S.P., available from Mallinkrodt Chemical Co.) and pyrogen-free water for injection, whereupon the solution was autoclaved and stored at 4° until use (storage limited to seven days);

(2) 10% $CaCl_2$, U.S.P., was diluted in an equal volume of sterile water immediately prior to use to yield a 5% solution (14 mg. $Ca^{++}$/ml);

(3) The dialysate was Cobe 43 acetate-based calcium-free dialysate or a conventional bicarbonate-based, calcium-free dialysate solution.

In one series of dialysis runs in accordance with the invention, a 34 year old white male had sustained multiple internal organ injuries as a result of an automobile accident. He required two exploratory laparotomies and an exploratory mediastinotomy during this first hospital day. Massive, nearly uncontrollable bleeding complicated his course, and by 30 hours he had required 75 units of blood transfusions.

The patient developed acute oliguric renal failure on the first hospital day. Subsequently, he developed acute pulmonary edema (pulmonary capillary wedge=31 mm Hg), acute G-I bleeding, thrombocytopenia (43,000=platelet), massive transfusion washout coagulopathy, and vigorous bleeding from all incision sites. Systemic manifestations of sepsis, included relative hypotension (B.P. 100/60), temperature of 40.2° C. and +blood cultures for gram negative rods.

Hemodialysis for extracellular volume removal was instituted early on day three. Over the next 15 hospital days a total of 8 hemodialyses with citrate regional anticoagulation were carried out. During this period of time additional patient problems included hepatic failure (bilirubin to 53.4 mg/dl), peritonitis, wound dehiscence and respiratory failure. Despite these conditions, each hemodialysis was accomplished without significant incident.

In more detail, the eight dialyses involved four four hour runs, one five hour run, one six hour run, and two eight hour runs. In two of the four hour runs and five hour run the acetate-based dialysate was employed, whereas in the remaining runs the bicarbonate dialysate was used.

In all cases a Cobe Century II dialyzer was used, with a C-D 4000 capillary dialyzer unit. The overall apparatus was of the type illustrated in the FIGURE. Blood flow rate was maintained throughout each run at 200 milliliters/minute, with trisodium citrate being infused at a rate of 2.5% of blood flow rate, and $CaCl_2$ solution at a rate of 0.5 milliliter/minute (7 milligrams $Ca^{++}$ ion/minute). Infusion rates of both substances were controlled using respective pressure insensitive occlusive pumps.

We claim:

1. A blood treatment method comprising the steps of:
   withdrawing blood from a patient at a rate of from about 100 to 300 milliliters per minute;
   preventing the coagulation of said withdrawn blood by infusing an anticoagulant substance into the blood, said anticoagulant substance consisting essentially of citrate anion and being infused at a level to provide up to about 10 millimoles of citrate anion per liter of blood;
   passing the withdrawn, citrate-infused blood through treatment apparatus concurrently with a toxin-removing dialysate for removing toxins from the blood;
   after passage of said blood through said apparatus, infusing into said blood a calcium compound in an amount to achieve a desired level of calcium ion in said blood; and
   returning the calcium-infused blood to said patient.

2. The method as set forth in claim 1, said blood removal rate being from about 150 to 250 milliliters per minute.

3. The method as set forth in claim 1, said dialysate being essentially calcium free.

4. The method as set forth in claim 1, said dialysate being selected from the acetate and bicarbonate-based dialysates.

5. The method as set forth in claim 1, said anticoagulant being infused at a level to infuse from about 2 to 8 millimoles of citrate anion per liter of blood.

6. The method as set forth in claim 5, said anticoagulant being infused at a level to infuse from about 2 to 6 millimoles of citrate anion per liter of blood.

7. The method as set forth in claim 1, said anticoagulant being trisodium citrate.$2H_2O$.

8. The method as set forth in claim 7, said trisodium citrate.$2H_2O$ being the sole anticoagulant substance employed.

9. The method as set forth in claim 1, said calcium ion being added to give a resultant blood level of calcium ion from about 8 to 12 milligrams per 100 milliliters of blood.

10. The method as set forth in claim 1, said anticoagulant being nearly isotonic relative to said blood.

11. The method as set forth in claim 1, including the step of passing said blood through filtering means.

12. A blood treatment method comprising the steps of:
   withdrawing blood from a human patient at a rate of from about 100 to 300 milliliters per minute;
   preventing the coagulation of said withdrawn blood by infusing an anticoagulant substance into the blood, said anticoagulant substance consisting essentially of trisodium citrate.$2H_2O$ which is only isotonic relative to said blood, said anticoagulant being infused at a level to provide up to about 10 millimoles of citrate anion per liter of blood;
   passing the withdrawn, citrate-infused blood through treatment apparatus concurrently with a calcium-free toxin-removing dialysate for removing toxins from the blood;
   after passage of said blood through said apparatus, infusing into said blood a calcium compound in an amount to achieve a desired level of calcium ion in said blood of from about 8 to 12 milligrams calcium ion per 100 milliliters of blood; and
   returning the calcium-infused blood to said patient.

* * * * *